US007297684B1

(12) United States Patent
Gleave et al.

(10) Patent No.: US 7,297,684 B1
(45) Date of Patent: Nov. 20, 2007

(54) ANTISENSE THERAPY FOR HORMONE-REGULATED TUMORS

(75) Inventors: Martin Gleave, Vancouver (CA); Hideaki Miyake, Chuo-Ku (JP)

(73) Assignee: The University of British Columbia, Vancouver (CA)

( * ) Notice: Subject to any disclaimer, the term of this patent is extended or adjusted under 35 U.S.C. 154(b) by 1363 days.

(21) Appl. No.: 09/619,908

(22) Filed: Jul. 19, 2000

Related U.S. Application Data

(60) Provisional application No. 60/144,495, filed on Jul. 19, 1999.

(51) Int. Cl.

| | |
|---|---|
| ***A01N 43/04*** | (2006.01) |
| ***A61K 31/70*** | (2006.01) |
| *C07H 21/04* | (2006.01) |
| *C12Q 1/68* | (2006.01) |
| *C12N 5/00* | (2006.01) |

(52) U.S. Cl. ...................... 514/44; 536/23.1; 536/24.5; 435/6; 435/375

(58) Field of Classification Search ................. 514/44; 435/325, 32.5, 375, 6; 536/24.5

See application file for complete search history.

(56) References Cited

U.S. PATENT DOCUMENTS 5,801,154 A * 9/1998 Baracchini et al. ........... 514/44
2003/0087857 A1 5/2003 Freier

FOREIGN PATENT DOCUMENTS

CA 2090702 3/1992
CA 2090705 3/1992

OTHER PUBLICATIONS

Reuters New release, Mar. 17, 2003. Lily, Isis Drug Fails in Trial.*

Sudhir Agrawal, Antisense Oligonucleotides: towards clinical trials, TIBTECH, Oct. 1996, vol. 14, pp. 376-387.*

Alan M. Gewirtz et al., Facilitating oligonucleotide delivery: Helping antisense deliver on its promise, Proc. Natl. Acad. Sci. USA, vol. 93, pp. 3161-3163, Apr. 16, 1996.*

Andrea D. Branch, A good antisense molecule is hard to find, TIBS 23—Feb. 1998, pp. 45-50.*

Ingo Tamm et al., Antisense therapy in oncology: new hope for an old idea? The Lancet, vol. 358, Aug. 11, 2001, pp. 489-497.*

Hideaki Miyake, Michael Pollak, and Martin E. Gleave, Castration-induced Up-Regulation of Insulin-like Growth Factor Binding Protein-5 Potentiates Insulin-like Growth Factor-I Activity and Accelerates Progression to Androgen Independence in Prostate Cancer Models, Cancer Research 60, 3058-3064, Jun. 1, 2000.

Christopher W. Gregory, Desok Kim, Ping Ye, A Joseph D'Ercole, Thomas G. Pretlow, James L. Mohler, and Frank S. French: Androgen Receptor Up-Regulates Insulin-Like Growth Factor Binding Protein-5 (IGFBP-5) Expression in a Human Prostate Cancer Xenograft, Endocrinology, vol. 140, No. 5, 1999.

Hideaki Miyake, Colleen Nelson,, Paul S. Rennie, and Martin E. Gleave; Overexpression of Insulin-Like Growth Factor Binding Protein-5 Helps Accelerate Progression to Androgen-Independence in the Human Prostate LNCaP Tumor Model through Activation of Phosphatidylinositol 3'-Kinase Pathway; Endocrinology, vol. 141, No. 6, 2000.

* cited by examiner

*Primary Examiner*—J. Douglas Schultz
*Assistant Examiner*—Dana Shin
(74) *Attorney, Agent, or Firm*—Marina Larson & Associates, LLC

(57) ABSTRACT

A method is provided for treating hormone-regulated tumors (for example, breast and prostatic tumors) in mammals, including humans, by administration of an antisense ODN which is complementary to a portion of the gene encoding IGFBP-5. Using the Shionogi tumor model in vitro and in vivo, the administration of such an ODN was shown to reduce proliferation of tumor cells, and also to delay the progression to androgen independence. Thus, treatment of prostate cancer in mammals, including humans, and delay of the progression of prostate tumors to androgen independence is accomplished by administering to the mammal a therapeutically effective amount of an antisense oligodeoxynucleotide which is complementary to a portion of the nucleic acid sequence encoding IGFBP-5 and which hybridizes with such a sequence to inhibit expression of IGFBP-5. Specific antisense ODN's which are suitable for use in the method are GACCACGCTGATCACCAT (Seq. ID. No. 1), which is derived from the murine gene sequence, and CGCGGTGAGCAACACCAT (Seq. ID. No. 3) and AGGTCATGCAGCAGCCGC (Seq. ID No 4), which are derived from the human gene sequence.

29 Claims, 7 Drawing Sheets

ANTISENSE THERAPY FOR HORMONE-REGULATED TUMORS

This application claims priority from U.S. Provisional Application No. 60/144,495 filed Jul. 19, 1999, which is incorporated herein by reference.

BACKGROUND OF THE INVENTION

This application relates to the treatment of hormone-regulated tumors (for example, breast and prostate tumors), making use of an antisense oligonucleotide that binds to insulin-like growth factor binding protein (IGFBP)-5.

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells, however thusfar no non-hormonal agent has improved survival. Oh et al., *J. Urol* 160: 1220-1229 (1998) Alternative approaches are therefore indicated.

Insulin-like growth factor (IGF)-I and IGF-II are potent mitogens for many normal and malignant cells. Accumulating evidence suggests that IGFs play an important role in the pathophysiology of prostatic disease and breast cancer. Boudon et al., *J. Clin. Endocrin. Metab.* 81: 612-617 (1996); Angelloz-Nicoud et al., *Endocrinology* 136: 5485-5492 (1995); Nickerson et al., *Endocrinology* 139: 807-810 (1998); Figueroa et al., *J. Urol.* 159: 1379-1383 (1998).

The biological response to IGF's is regulated by various factors, including IGFBPs. To date, six IGFBPs have been identified whose function is believed to involve modulation of the biological actions of the IGFs through high affinity interactions. Rajaram et al., *Endocrin. Rev.* 18: 801-813 (1997). However, some evidence suggests biological activity for IGFBPs that are independent of IGFs, Id., Andress et al., *J. Biol. Chem.* 267: 22467-22472 (1992); Oh et al., *J. Biol. Chem.* 268: 14964-14971 (1993), and both stimulatory and inhibitory effects of IGFBPs on cell proliferation have been reported under various experimental conditions. Andress et al., supra; Elgin et al., *Proc. Nat'l. Acad. Sci.* (*USA*), 84, 3254-3258 (1987); Huynh et al., *J. Biol. Chem.* 271: 1016-1021 (1996); Damon et al., *Endocrinology* 139: 3456-3464 (1998). Thus, the precise function role of IGFBPs remains controversial. Because of this, while the reported results implicate IGF in prostate and breast cancer, they do not clearly suggest a therapeutic approach based upon this involvement.

The present invention utilizes antisense oligodeoxynucleotides (ODNs) targeted to IGFBP-5 as a treatment for prostate and breast cancer. Antisense ODNs are chemically modified stretches of single-stranded DNA that are complementary to mRNA regions of a target gene, and thereby effectively inhibit gene expression by forming RNA/DNA duplexes. Figueroa, et al., *J. Urol,* 159:1379-1383 (1998). Phosphorothioate ODNs are stabilized to resist nuclease digestion by substituting one of the nonbridging phosphoryl oxygen of DNA with a sulfur. Recently, several antisense ODNs specifically targeted against genes involved in neoplastic progression have been evaluated both in vitro and in vivo, and demonstrated the efficacy of antisense strategy as potential therapeutic agents. Monia, et al. *Nature Med.* 2: 668-675 (1996.); Cucco, et al., *Cancer Res.* 56: 4332-4337 (1996); Ziegler, et al., *J. Natl. Cancer Inst.* 89: 1027-1036 (1997); Jansen, et al., *Nature Med.* 4: 232-234 (1998).

SUMMARY OF THE INVENTION

The present invention provides a method for treating hormone-regulated tumors (for example, breast and prostatic tumors) in mammals, including humans, by administration of an antisense ODN which is complementary to a portion of the gene encoding IGFBP-5. Using the Shionogi tumor model in vitro and in vivo, the administration of such an ODN was shown to reduce proliferation of tumor cells, and also to delay the progression to androgen independence. Thus, in accordance with the invention we provide methods for treatment of prostate cancer in mammals, including humans, and for delaying the progression of prostate tumors to androgen independence comprising the step of administering to the mammal a therapeutically effective amount of an antisense oligodeoxynucleotide which is complementary to a portion of the nucleic acid sequence encoding IGFBP-5 and which hybridizes with such a sequence to inhibit expression of IGFBP-5. Specific antisense ODN's which are suitable for use in the method are GACCACGCTGATCACCAT (Seq. ID. No. 1), which is derived from the murine gene sequence, and CGCGGTGAGCAACACCAT (Seq. ID. No. 3) and AGGTCATGCAGCAGCCGC (Seq. ID No 4), which are derived from the human gene sequence.

DETAILED DESCRIPTION OF THE INVENTION

Figure 1:
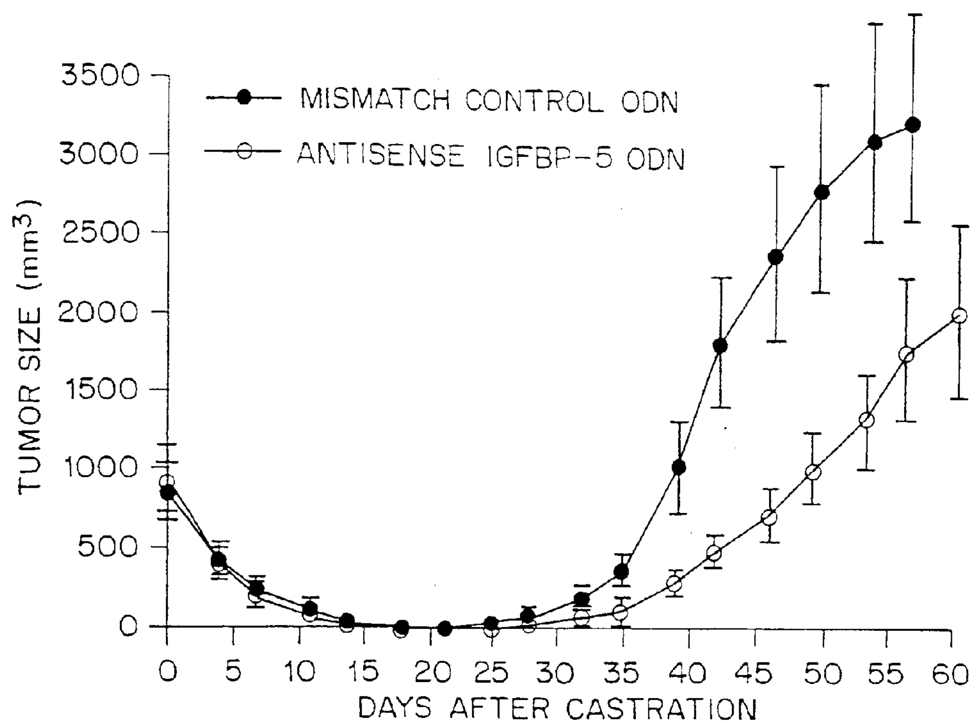
FIG. 1 shows the effects of antisense IGFBP-5 ODN in decreasing the regrowth of tumor cells following surgical androgen withdrawal.

The present invention provides a method for delaying the progression of hormone-regulated (prostatic or breast)

tumor cells to hormone (e.g. androgen or estrogen) independence, a therapeutic method for the treatment of individuals, including humans, suffering from hormone regulated cancers, such as breast or prostate cancer, and therapeutic agents effective for use in such methods. In addition, the compositions of the invention can be used to inhibit or delay the growth and metastatic progression of prostate, breast and other IGF-1 sensitive tumors in bone. The therapeutic method of the invention will most commonly be used in the treatment of individuals with advanced breast or prostate cancer.

In accordance with a first embodiment of the invention, the progression of androgen-sensitive prostatic cancer cells to androgen-independence can be delayed by inhibiting the expression of IGFBP-5 by the cells. Experiments were performed in vitro and in vivo in the Shionogi tumor model. The Shionogi tumor model is a xenograft of an androgen-dependent mouse mammary carcinoma that grows subcutaneously in male syngeneic hosts. Shionogi tumor cells are highly tumorigenic and locally invasive. The cells have been shown to respond to androgen withdrawal in a manner which mimics the observed behavior of prostatic tumor cells, and have been accepted as a valid model for prostate cancer in humans. (Bruchovsky et al., *Cancer Res.* 50: 2275-2282 (1990); Rennie et al., *Cancer res.* 48: 6309-6312 (1988); Bruchovsky et al., *Cell* 13: 272-280 (1978); Gleave et al., in *Genitourinary Oncology*, pp. 367-378, Lange et al. eds., Lippencott (1997); Gleave et al., *J. Urol.* 157: 1727-1730 (1997); Bruchovsky et al., *The Prostate* 6: 13-21 (1996). Thus, androgen withdrawal precipitates apoptosis and tumor regression in a highly reproducible manner. Further, changes in expression of peptides such as TRPM-2 and Bcl-2 in human prostate cancer following castration and during progression to androgen-independence are similar to those observed in Shionogi tumor cells. Because of these similarities, the Shionogi tumor model mimics human prostate cancer and provides a very useful model for the evaluation of the ability of compounds to delay the onset of androgen-independence. Despite complete tumor regression after castration, rapidly growing androgen-independent Shionogi tumors invariably recur after one month, which provides a reliable end point to evaluate agents which can delay the progression to androgen-independence.

In the study leading to the present invention, we initially characterized the changes of IGFBPs expression in the Shionogi tumor model after castration and during AI progression. Northern blot analyses were used to characterize changes in IGFBPs mRNA expression in AD intact tumors before castration, regressing tumors 4 and 7 days after castration, and AI recurrent tumors 28 days after castration. Various patterns of changes in IGFBP-2, -3, -4, and -5 mRNA expression were observed. IGFBP-1 and IGFBP-6 mRNAs are undetectable in the Shionogi tumor model. Of the IGFBPs expressed in Shionogi tumors, the most dramatic changes in expression were observed with IGFBP-5. Despite undetectable levels in AD intact tumors, IGFBP-5 expression is highly upregulated after castration, and remains highly expressed in AI tumors. The pattern of IGFBP-5 upregulation in the Shionogi tumor model during AI progression is similar to that in rat prostate (Angelloz-Nicoud, supra), and human prostate cancer (Figueroa, supra), and therefore supports use of this model to evaluate the effect of adjuvant antisense IGFBP-5 therapy on progression to androgen-independence.

To study the functional significance of this upregulation, we tested the effects of antisense IGFBP-5 ODN on IGF-1 mediated cell growth both in vitro and in vivo using the Shionogi tumor model. These tests were carried out using an antisense ODN directed against the murine IGFBP-5 gene. These experiments showed that phosphorothioate antisense IGFBP-5 ODN corresponding to the mouse IGFBP-5 translation initiation site inhibited expression of IGFBP-5 mRNA in a dose-dependent manner. Sequence specificity was confirmed using a 2-base IGFBP-5 mismatch ODN, which had no effects on IGFBP-5 mRNA expression in Shionogi tumor cells. Furthermore, we demonstrated that antisense IGFBP-5 ODN decreased IGFBP-5 expression in a target specific manner; that is, the expression of other mRNAs, including IGFBP-2, -3, and -4, were not affected by antisense IGFBP-5 ODN treatment.

Antisense IGFBP-5 ODN inhibits cell proliferation and induces cell cycle arrest in Shionogi tumor cells in a time- and dose-dependent manner. Antisense IGFBP-5 ODN treatment does not appear to induce apoptosis either in vitro or in vivo, which suggests that antisense IGFBP-5 ODN activity occurs via inhibition of cell proliferation rather than induction of apoptosis. Further, it was observed that the growth-inhibitory effects of antisense IGFBP-5 ODN can be reversed by exogenous IGF-1 and that antisense IGFBP-5 ODN treatment caused no additional inhibition of cell proliferation when IGF-1 activity was neutralized by anti-IGF-1 antibodies. We also found that antisense IGFBP-5 ODN inhibited MAPK activity, that this inhibition could also be reversed by exogenous IGF-1, and that antisense IGFBP-5 ODN had no independent inhibitory effect on MAPK activity when IGF-1 was neutralized by anti-IGF-1 antibodies. Collectively, these findings demonstrate that antisense IGFBP-5 ODN inhibited the cell proliferation, at least in part, through an IGF-I-dependent mechanism involving inactivation of MAPK.

Based on this in vitro data, we hypothesized that targeting IGFBP-5 upregulation precipitated by androgen using antisense strategy might inhibit progression to androgen-independence. In our in vivo experiments, administration of antisense IGFBP-5 ODN after castration delayed time to AI progression and inhibited AI recurrent tumor growth. Consistent with our in vitro treatments, in vivo treatment of mice bearing Shionogi tumors with antisense IGFBP-5 ODN also inhibited the IGFBP-5 mRNA expression. These findings illustrate that in vivo systemic administration of ODN can result in sequence specific down-regulation of a target gene in tumor cells.

Although insulin-like growth factor (IGF) binding protein-5 (IGFBP-5) is highly up-regulated in normal and malignant prostate tissues after androgen withdrawal, its functional role in castration-induced apoptosis and androgen-independent progression remains undefined. To analyze the functional significance of IGFBP-5 overexpression in IGF-I-mediated mitogenesis and progression to androgen-independence, IGFBP-5-overexpressing human androgen-dependent LNCaP prostate cancer cells were generated by stable transfection. The growth rates of IGFBP-5 transfected LNCaP cells were significantly faster compared to either the parental or vector-only transfected LNCaP cells in both the presence and absence of dihydrotestosterone. IGFBP-5-induced increases in LNCaP cell proliferation occurs through both IGF-I-dependent and -independent pathways, with corresponding increases in the cyclin D1 mRNA expression and the fraction of cells in S+G2/M phases of the cell cycle. Changes in Akt/protein kinase B (PKB), a downstream component of phosphatidylinositol 3'-kinase (PI3K) pathway, in the LNCaP sublines also paralleled changes in their growth rates. Although treatment with a PI3K inhibitor induced apoptosis in both control and IGFBP-5-overexpressing LNCaP cells, this PI3K inhibitor-induced apoptosis was prevented by exogenous IGF-I treatment only in IGFBP-5 transfectants, suggesting that IGFBP-5 overexpression can potentiate the antiapoptotic effects of IGF-I. Furthermore, tumor growth and serum PSA levels increased several fold faster in mice bearing IGFBP-5-transfected LNCaP tumors after castration despite having similar tumor incidence and tumor growth rates with controls when grown in intact mice before castration. Collectively, these data suggest that IGFBP-5 overexpression in prostate cancer cells after castration is an adaptive cell survival mechanism that helps potentiate the antiapoptotic and mitogenic effects of IGF-I, thereby accelerating progression to androgen-independence through activation of the PI3K-Akt/PKB signaling pathway.

A rational strategy to delay AI progression should be based on molecular mechanisms and would target the adaptive changes in gene expression precipitated by androgen withdrawal, rather than the conventional approach of treating patients with established hormone refractory disease. Integration and appropriate timing of combination therapies, based on biological mechanism of progression and castration-induced changes in gene expression, may provide means to inhibit AI progression in a major way. The present study provides direct evidence to support a functional role for IGFBP-5 in AI progression, and that reduction of IGFBP-5 gene expression using antisense IGFBP-5 ODN delays recurrence and growth of AI tumors.

The treatment of the present invention can be used individually. However, the antisense ODNs are preferably utilized in combination with other therapies, that result in androgen-withdrawal. Thus, in accordance a further aspect of with the invention, therapeutic treatment of individuals, including human individuals, suffering from prostate cancer is achieved by initiating androgen-withdrawal to induce apoptotic cell death of prostatic tumor cells in the individual, and administering to the individual a composition effective to inhibit expression of IGBFP-5 by the tumor cells, thereby delaying the progression of prostatic tumor cells to an androgen-independent state in an individual. In view of the expression of IGFBP-5 in bone, IGF-1 and IGFBP-5 mediated tumor cells growth may also play a substantial role in promoting growth of IGF-1 sensitive metastatic tumor cells in bone. This growth can be prevented through the use of the antisense IGBFP-5 ODN of the invention, thus inhibiting or delaying the progression of metastatic disease.

Initiation of androgen withdrawal may be accomplished via surgical (removal of both testicles) or medical (drug-induced suppression of testosterone) castration, which is currently indicated for treatment of prostate cancer. Medical castration can be achieved with various regimens, including LHRH agents and antiandrogens. Gleave et al. *CMAJ* 160: 225-232 (1999). Intermittent therapy in which reversible androgen withdrawal is effected is described in Gleave et al. *Eur. Urol.* 34, Supp 3: 37-41 91998). Hormone withdrawal in the case of breast cancer can be achieved through drug therapy with anti-estrogenics such as tamoxifen.

The inhibition of IGBFP-5 expression may be transient, and should occur following androgen withdrawal. In humans, this means that inhibition of expression should be effective starting within weeks of androgen withdrawal and extending for about 3 to 6 months. This may require multiple doses to accomplish. It will be appreciated, however, that the period of time may be more prolonged, starting before castration and expending for substantial time afterwards without departing from the scope of the invention.

The ODN used in the tests described above and in the examples below (Seq. ID. No. 1) is complementary to a portion of the murine IGFBP-5 gene overlaps with the translation initiation site. Other ODN species might also be employed, including somewhat long or somewhat shorter ODN species (for example in the range of 15 to 30 nt) that overlap with the translation initiation site, and ODN species that overlap with the translation termination site. Intermediate ODN's may also be effective, and can be screened for their ability to provide adequate levels of IGFBP-5 inhibition using the expression assay described in the examples. In selecting the antisense ODN for use, it is desirable to avoid substantial complementarity with other IGFBPs, since inhibition of expression of these other proteins might lead to undesirable side effects. The nucleic acid sequence of mouse IGFBP-5 from which such ODN can be derived is given by SEQ ID No. 13.

Figure 9:
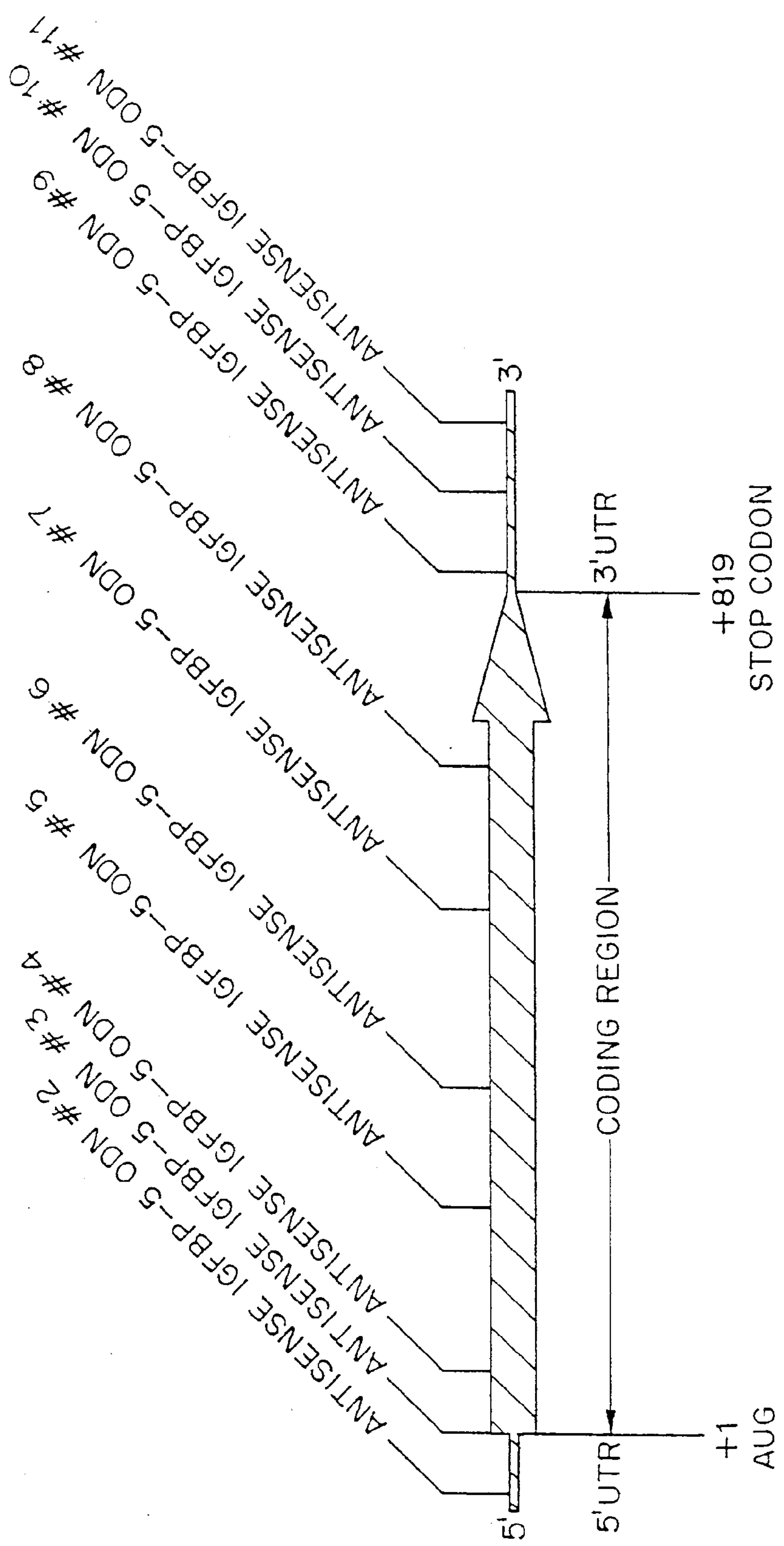
FIG. 9 shows a schematic representation of the nucleotide sequence for human IGBFP-5, with the locations of 10 antisense ODN's indicated.

To apply the invention in other mammals, including humans, therapeutic antisense ODNs are derived from the corresponding locations in the IGFBP-5 gene of the target species. For example, in the case of humans, the sequence of the IGFBP-5 gene is known from Kiefer et al., *Biochem. Biophys Res. Commun.* 176: 219 (1991), Accession No. M65062 for human and James et al., *J. Biol. Chem.* 258: 22305 (1993), Accession No. L12447 for mouse. FIG. 9 shows the locations of several antisense ODN's which were tested for the ability to inhibit expression of IGFBP-5 in humans. Of the sequences tested using the procedures set forth in the examples, the antisense oligonucleotide with the greatest activity has the sequence given by Seq. ID. No. 3. This ODN overlaps with the translation initiation site of human IGFBP-5. As in the case of the mouse model, other human therapeutic antisense ODNs may be employed, including somewhat long or somewhat shorter ODN species (for example in the range of 15 to 30 nt) that overlap with or are located near the translation initiation site (for example SEQ ID No. 4), and ODN species that overlap with the translation termination site (for example SEQ ID No. 10). Intermediate ODN's may also be effective, and can be screened for their ability to provide adequate levels of IGFBP-5 inhibition using the expression assay described in the examples. In selecting the antisense ODN for use, it is desirable to avoid substantial complementarity with other IGFBPs, since inhibition of expression of these other proteins might lead to undesirable side effects. The complete sequence of human IGFBP-5 from which other antisense ODN can be derived is given by SEQ ID No. 14. SEQ ID Nos. 15-66 list additional antisense ODN sequences designed from the sequence of human IGFBP-5.

The ODNs employed may be modified to increase the stability of the ODN in vivo. For example, the ODNs may be employed as phosphorothioate derivatives (replacement of a non-bridging phosphoryl oxygens atoms with a sulfur atom) which have increased resistance to nuclease digestion. Increased ODN stability can also be achieved using molecules with 2-methoxyethyl substituted backbones.

Administration of antisense ODNs can be carried out using the various mechanisms known in the art, including naked administration and administration in pharmaceutically acceptable carriers. For example, lipid carriers for antisense delivery are described in U.S. Pat. Nos. 5,855,911 and 5,417,978 which are incorporated herein by reference. In general, the antisense is administered by intravenous, intraperitoneal, subcutaneous or oral routes.

The amount of antisense ODN administered is one effective to inhibit the expression of IGBFP-5 in breast cancer or prostatic cells. It will be appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels.

The method for treating prostate or breast cancer in accordance with the invention may further include administration of chemotherapy agents and/or additional antisense ODNs directed at different targets. For example, conventional chemotherapy agents such as taxol (paclitaxel or docitaxel) and mitoxanthrone may be used. Similarly, combinations of antisense IGFBP-5 ODN with other antisense species such as antisense Bcl-2 ODN or TRPM-2 ODN may be used.

The invention will now be further described with reference to the following, non-limiting examples.

EXAMPLE 1

Shionogi tumor model experiments were performed using cells from the Toronto subline of transplantable SC-115 AD mouse mammary carcinoma, and maintained in Dulbecco's modified Eagle medium (Life Technologies, Inc., Gaithersburg, Md.) supplemented with 5% heat-inactivated fetal calf serum. For in vivo studies, approximately $5\times10^6$ cells of the Shionogi carcinoma were injected subcutaneously in adult male DD/S strain mice. When the Shionogi tumors became 1 to 2 cm in diameter, usually 2 to 3 weeks after injection, castration was performed through an abdominal incision under methoxyflurane anesthesia. Details of the maintenance of mice, tumor stock and operative procedures have been previously described. Bruchovsky et al., *Cancer Res.* 5); 2275-2282 (1990); Rennie et al., *Cancer Res.* 48: 6309-6312 (1988); Bruchovsky et al., *Cell* 13: 272-280 (1978).

Mice were randomly selected for treatment with murine phosphorothioate antisense IGFBP-5 ODN (Seq. ID No. 1) or a mismatch control having the sequence GACCACGCTCATGACCAT (Seq. ID No. 12) which is two bases different in sequence from the antisense IGFBP-5 ODN. Each experimental group consisted of 8 mice. Beginning the day of castration, 15 mg/kg of antisense IGFBP-5 or mismatch control ODN were injected intraperitoneally once daily into each mouse for 50 days. Tumor volume was measured twice weekly, and calculated by the formula length X width X depth X 0.5236. Gleave, *Cancer Res.* 52: 1598-1605 (1992). Data points were reported as average tumor volumes ± standard deviation.

The results of this study are shown in FIG. 1. Antisense IGFBP-5 ODN treatment delayed recurrence of AI tumors compared to mismatch control ODN treatment. Although AI tumors recurred in all mice in both groups during an observation period of 60 days post-castration, median time to first palpable AI recurrence increased by 25% from 28 to 35 days in mice treated with antisense IGFBP-5 vs mismatch control ODN. Mice required sacrifice when tumor mass increased above 3 $cm^3$ or 10% of body weight. Growth of recurrent AI tumors was substantially inhibited in antisense IGFBP-5 ODN treatment group compared to the mismatch control ODN group. Time to sacrifice of mice was significantly prolonged in the antisense IGFBP-5 ODN treatment group, all mice required sacrifice in mismatch ODN group after a median of 53 days compared to only 1 of 8 mice in antisense IGFBP-5 ODN treatment group after 60 days ($p<0.05$).

EXAMPLE 2

Figure 2:
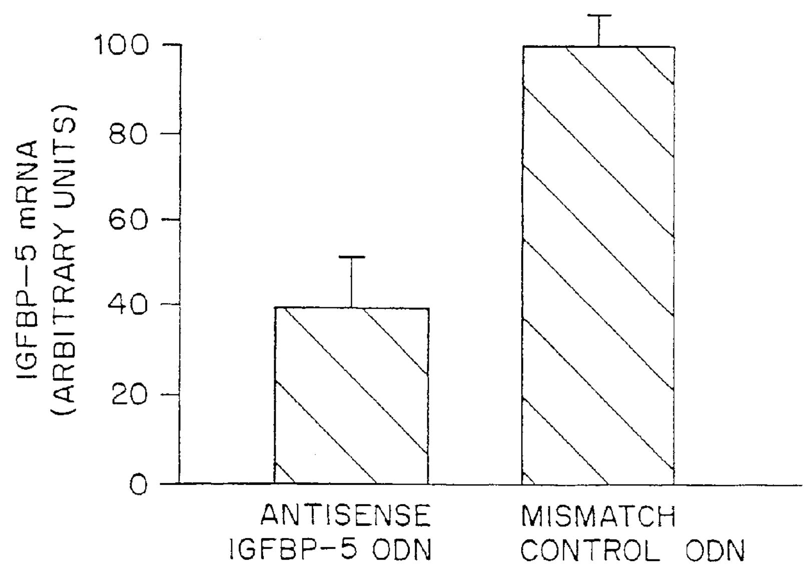
FIG. 2 shows the reduction in IGFBP-5 mRNA following treatment with antisense IGFBP-5 ODN in vivo.

To examine the effects of in vivo ODN treatment on levels of IGFBP-5 mRNA, Northern blot analysis was performed on Shionogi tumor tissue from mice. Mice were treated daily, beginning the day of castration, with 15 mg/kg of antisense IGFBP-5 ODN (n=3) or the mismatch control (n=3) by intraperitoneal injection. On the fourth day after castration, tumor tissues were harvested and analyzed by Northern blot for IGFBP-5 mRNA. Antisense IGFBP-5 ODN resulted in a 61% reduction in IGFBP-5 mRNA levels in Shionogi tumors compared to mismatch control ODN treated tumors. (FIG. 2).

EXAMPLE 3

The sequence selectivity of the antisense IGFBP-5 ODN (Seq. ID. No. 1) was confirmed by comparing expression levels of IGFBP-5 mRNA in Shionogi tumor cells maintained in vitro, after treatment with varying levels of antisense IGFBP-5 ODN (Seq. ID No. 1) or a mismatch control (Seq. ID. No. 12). To facilitate uptake of the ODNs into the cells, the ODNs were formulated in a cationic lipid carrier (Lipofectin™, (Life Technologies, Inc.)). Cells were treated twice over a period of two days using the following protocol. Cells were preincubated for 20 minutes with 4 μg/ml of lipofectin in serum free OPTI-MEM™ (Life Technologies, Inc.) and then incubated with the medium containing the selected concentration of ODN and lipofectin for four hours. The medium was then replaced with the standard culture medium described in Example 1.

Figure 3:
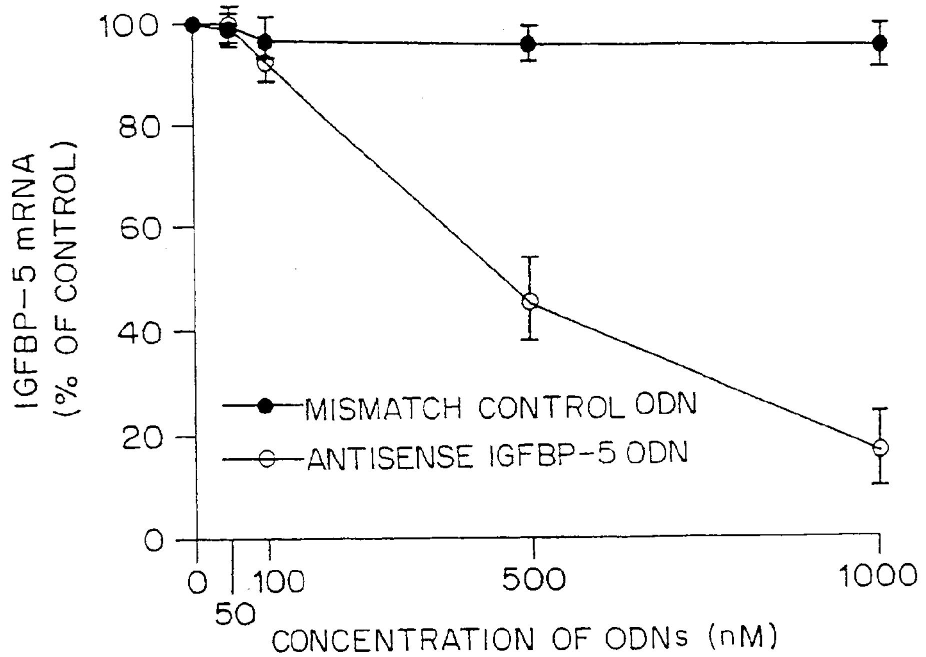
FIG. 3 shows the dosage-dependence of the reduction in IGFBP-5 mRNA following treatment with antisense IGFBP-5 ODN in vitro.

The amount of IGFBP-5 mRNA in the cells was evaluated using Northern blot analysis. As shown in FIG. 3, daily treatment of Shionogi cells with antisense IGFBP-5 ODN (Seq. ID No. 1) at levels of 50, 100, 500 or 1000 nM reduced IGFBP-5 mRNA levels in a dose dependent manner by 0, 7, 54 or 83%, respectively. In contrast, IGFBP-5 mRNA levels were not affected by the mismatch ODN (Seq. ID. No. 3) at any of the employed concentrations. Thus, the affect of antisense IGFBP-5 ODN is apparently sequence specific.

To further analyze the specificity of antisense IGFBP-5 ODN, Northern blotting was performed after treatment of Shionogi tumor cells with 1 μM antisense IGFBP-5 ODN (Seq. ID. No. 1) to quantify changes in expression other IGFBP (IGFBP-2, -3, and -4) genes, which share significant sequence homology with IGFBP-5. Antisense IGFBP-5 ODN markedly reduced IGFBP-5 mRNA expression, but no effects were observed on IGFBP-2, -3, and -4 expression levels. Collectively these data demonstrate that antisense IGFBP-5 ODN used in these studies induce sequence-specific, gene-specific, and dose-dependent downregulation of its target gene.

EXAMPLE 4

Figure 4:
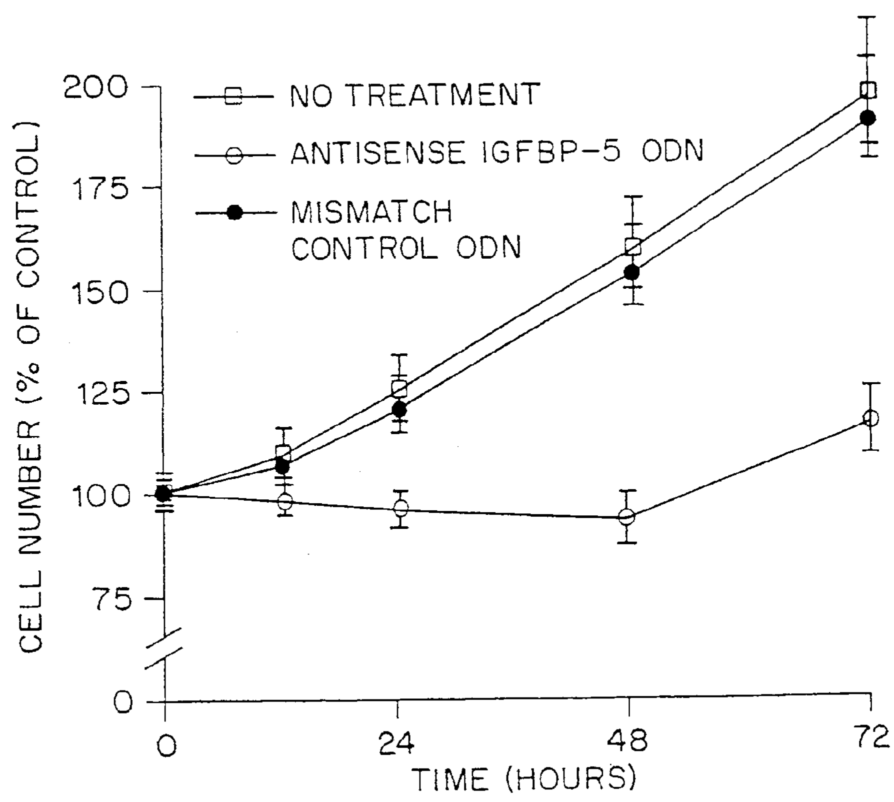
FIG. 4 shows the number of cells present following treatment with antisense IGFBP-5 ODN as a function of time.

To determine the effects of antisense IGFBP-5 ODN on cell proliferation, we treated Shionogi tumor cells once daily with either 1 μM antisense IGFBP-5 or mismatch control ODN for 2 days, and determined cell number over a 72 h period. Antisense IGFBP-5 ODN treatment of cells resulted in significant inhibition of Shionogi tumor cell proliferation over this 72 h, whereas cell growth was not influenced by treatment with mismatch control ODN (FIG. 4).

Figure 5:
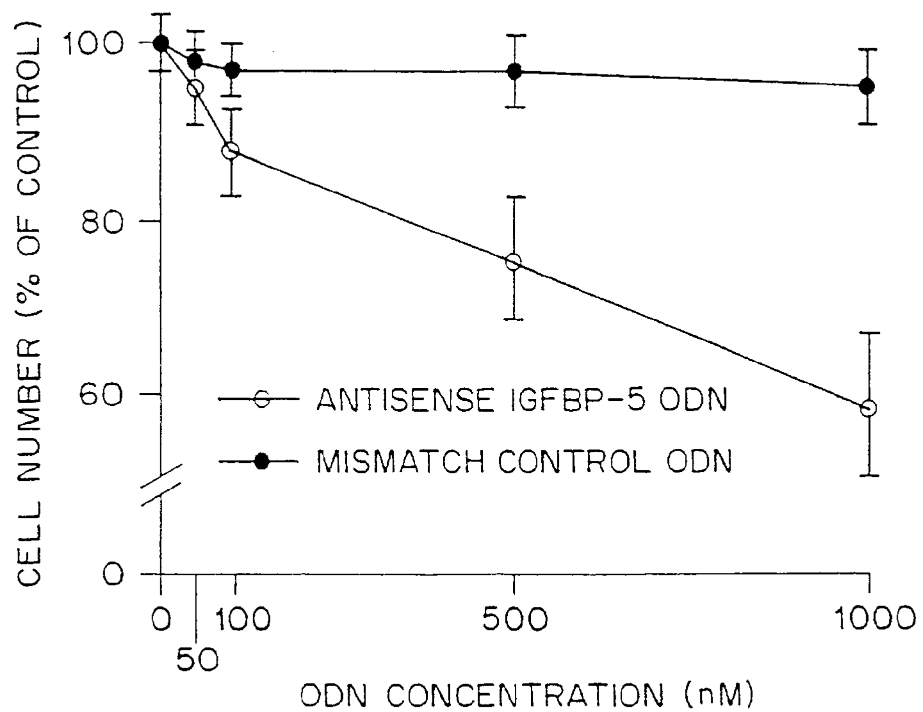
FIG. 5 shows the number of cells present following treatment with antisense IGFBP-5 ODN as a function of concentration.

The effects of antisense IGFBP-5 ODN on cell proliferation were also found to be dose-dependent over a concentration range between 100 and 1000 nM (FIG. 5). These antiproliferative effects were directly correlated with the degree of IGFBP-5 mRNA reduction in Shionogi tumor cells by antisense IGFBP-5 ODN. In contrast, no significant effects were observed on cell proliferation with mismatch control ODN at any of the employed concentrations.

Figure 6:
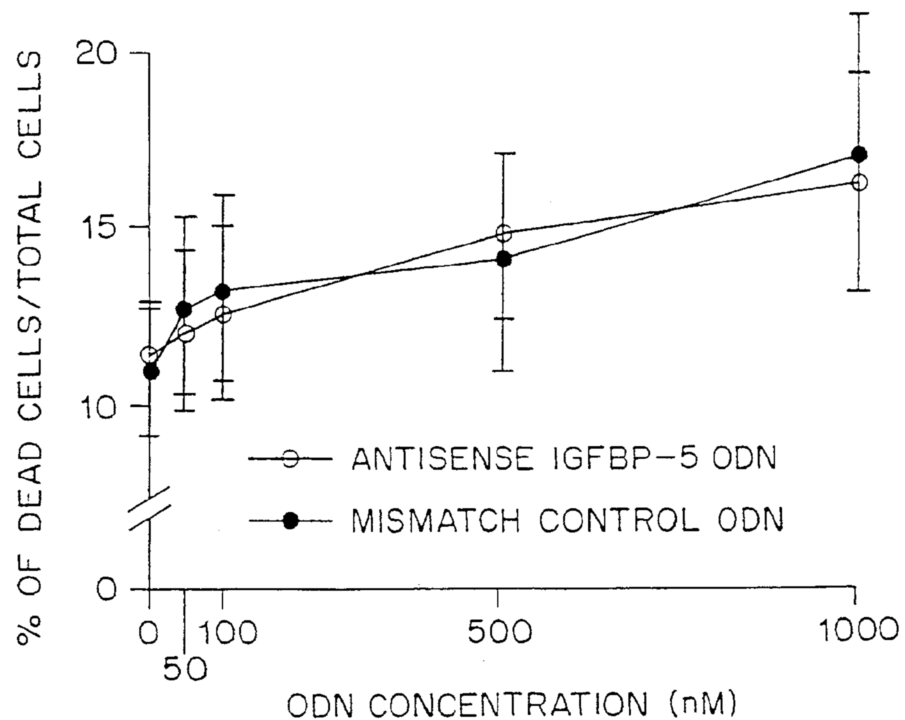
FIG. 6 shows the proportion of dead cells in a sample treated with antisense IGFBP-5 ODN.

To exclude the possibility that antisense IGFBP-5 ODN acted as a cell death factor through induction of apoptosis, the number of live and dead cells were counted after antisense or mismatch IGFBP-5 ODN treatment. Live and dead Shionogi cells from each subculture were counted using trypan blue 48 h after ODN treatment, and the ratio of dead/total cells was calculated. Each assay was performed in triplicate. The observed ratio of dead cells to total cell number of antisense IGFBP-5 ODN-treated cells was not significantly different from that of mismatch control ODN-treated cells (FIG. 6). Hence, differences in cell number after antisense IGFBP-5 ODN treatment are not the result of enhanced apoptosis.

EXAMPLE 5

To analyze the relationship between IGFBP-5 and IGF-I in the regulation of Shionogi tumor cell growth, the effects of antisense IGFBP-5 ODN treatment on Shionogi tumor cell proliferation with anti-IGF-I antibodies and/or recombinant IGF-I were evaluated. In a first experiment, the in vitro effects of antisense IGFBP-5 ODN, anti-IGF-I antibody (Upstate Biotechnology, Lake Placid, N.Y.), and/or recombinant IGF-I (Sigma Chemical Co., St. Louis, Mo.) on growth of Shionogi tumor cells were assessed by the MTT assay as described previously Miyake, et al., *Oncogene* 16: 933-943 (1998). Briefly, $1\times10^4$ cells were seeded in each well of 96-well microtiter plates and allowed to attach overnight. Cells were then treated once daily with various concentrations of ODN for 2 days in the media containing 5 nM recombinant IGF-I or 10 μg/ml anti-IGF-I antibody. 48 h after ODN treatment, 20 μl of 5 mg/ml MTT (Sigma Chemical Co.) in PBS was added to each well, followed by incubation for 4 h at 37° C. The formazan crystals were then dissolved in dimethyl sulfoxide. The optical density was determined with a microculture plate reader (Becton Dickinson Labware, Lincoln Park, N.J.) at 540 nm. Absorbance values were normalized to the values obtained for the vehicle-treated cells to determine the percent of survival. Each assay was performed in triplicate.

Figure 7:
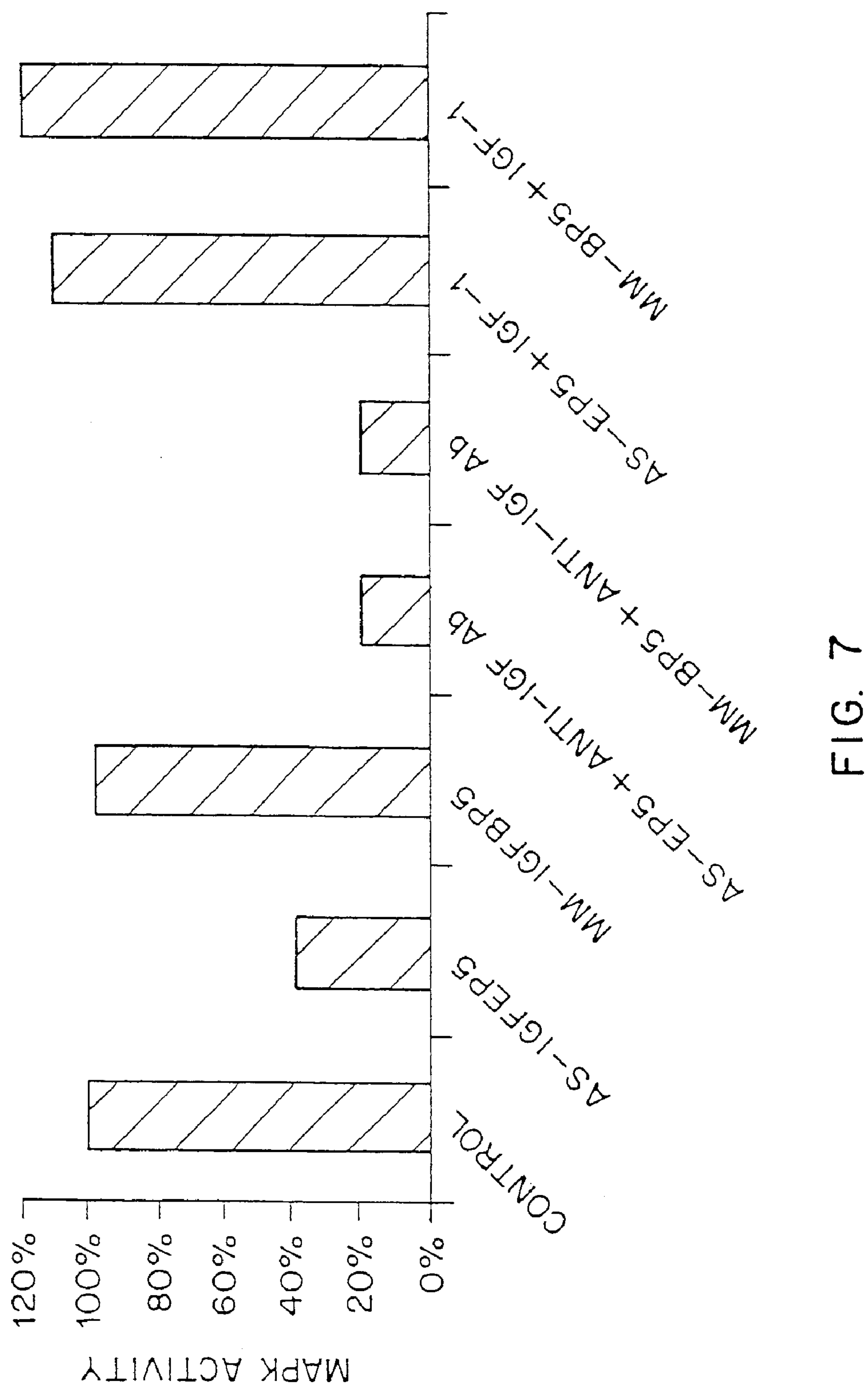
FIG. 7 shows the effects of antisense IGFBP-5 ODN in relation to IGF-1 and anti-IGF-1 antibody.

As shown in FIG. 7, recombinant IGF-I increased Shionogi tumor cell proliferation, while anti IGF-1 neutralizing antibodies inhibited Shionogi cell growth by 60%. Furthermore, inhibition of cell proliferation by antisense IGFBP-5 ODN could be reversed by exogenous recombinant IGF-I treatment. Addition of antisense IGFBP-5 ODN with anti IGF-1 neutralizing antibodies did not add to the inhibitory effects of anti IGF-1 neutralizing antibodies alone. Collectively, these findings support an enhancing and IGF-I-dependent effect of IGFBP-5 on the cell proliferation.

Because MAPK is one of the most potent pathways for IGF-I signal transduction, we measured the effects of antisense IGFBP-5 and anti IGF-1 neutralizing antibodies on MAPK activity in Shionogi tumor cells. Mitogen-activated protein kinase (MAPK) activity was measured using a MAP Kinase Assay Kit (New England Biolabs, Beverly, Mass.). Briefly, the cells were washed with PBS, lysed in lysis buffer, sonicated, and microcentrifuged for 20 min at 4° C. The supernatants was incubated with 1:100-diluted anti-phospho-MAPK antibody for 4 h. Protein A-agarose beads were then added and incubated for another 3 h. The pellets were washed twice with ice-cold lysis buffer and twice with kinase buffer. The pellets were incubated with 100 mM ATP and 20 mg/ml Elk1 fusion protein, a substrate of MAPK, for 30 min at 30° C. Samples were boiled, separated by electrophoresis through a 10% SDS-polyacrylamide gel, and transferred to polyvinylidene difluoride membranes. The membranes were incubated for 1 h at room temperature in blocking buffer, and then probed with 1:1000-diluted anti-phospho-Elk1 antibody. After wash, the membranes were incubated with a 1:1000-diluted horseradish peroxidase-conjugated anti-rabbit immunoglobulin. The immunoreactivity of phosphorylated Elk1 was determined using an ECL chemiluminescence kit.

Observed changes in MAPK activity mirrored changes in cell proliferation induced by these agents; that is, antisense IGFBP-5 ODN reduced MAPK activity, this antisense IGFBP-5-induced decrease in MAPK activity effect could be reversed by recombinant IGF-I, and antisense IGFBP-5 had no additional inhibitory effect on MAPK activity when the mitogenic effects of IGF-1 were neutralized by anti-IGF-1 antibodies.

EXAMPLE 6

To examine effects of changes in IGFBP-5 expression levels on cell cycle regulation, flow cytometric analysis was performed in Shionogi tumor cells. The flow cytometric analysis of propidium iodide-stained nuclei was performed as described previously Miyake, supra. Briefly, Shionogi tumor cells were plated at a density of $5\times10^6$ cells in 6-cm dishes, and treated as described above. The cells were trypsinized 48 h after ODN treatment, washed twice with PBS, and fixed in 70% ethanol for 5 h at 4° C. The fixed cells were washed twice with PBS, incubated with 1 μg/ml RNaseA (Sigma Chemical Co.) for 1 h at 37° C. and stained with 5 μg/ml propidium iodide (Sigma Chemical Co.) for 1 h at room temperature. The stained cells were analyzed for relative DNA content on a FACScan™ (Becton Dickinson Labware).

Figure 8:
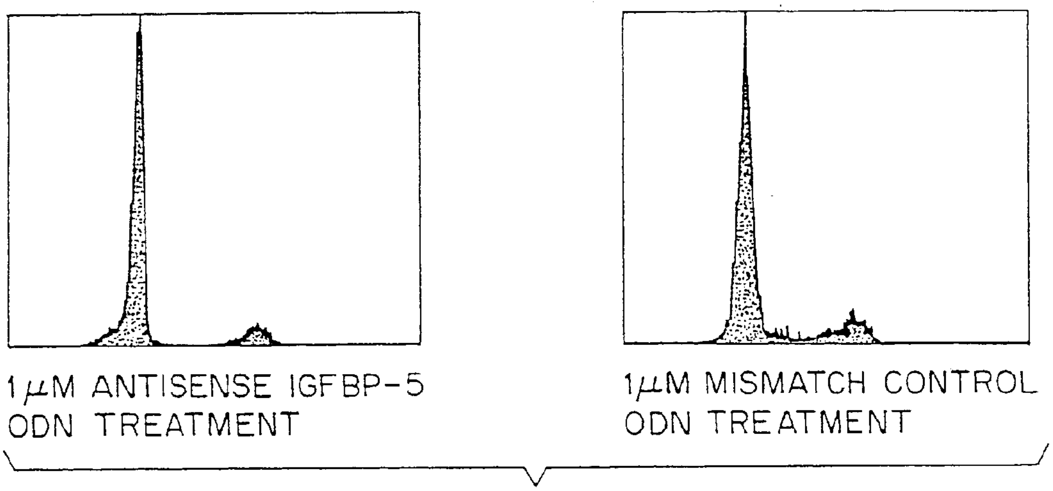
FIG. 8 shows flow cytometry results for cells treated with antisense IGFBP-5 ODN.

As shown in FIG. 8, decreases in IGFBP-5 levels induced by antisense IGFBP-5 ODN treatment resulted in G1 cell cycle arrest, thereby reducing the fraction of cells in the S+G2/M phases by more than 50% compared to mismatch control ODN treatment.

EXAMPLE 7

Figure 10:
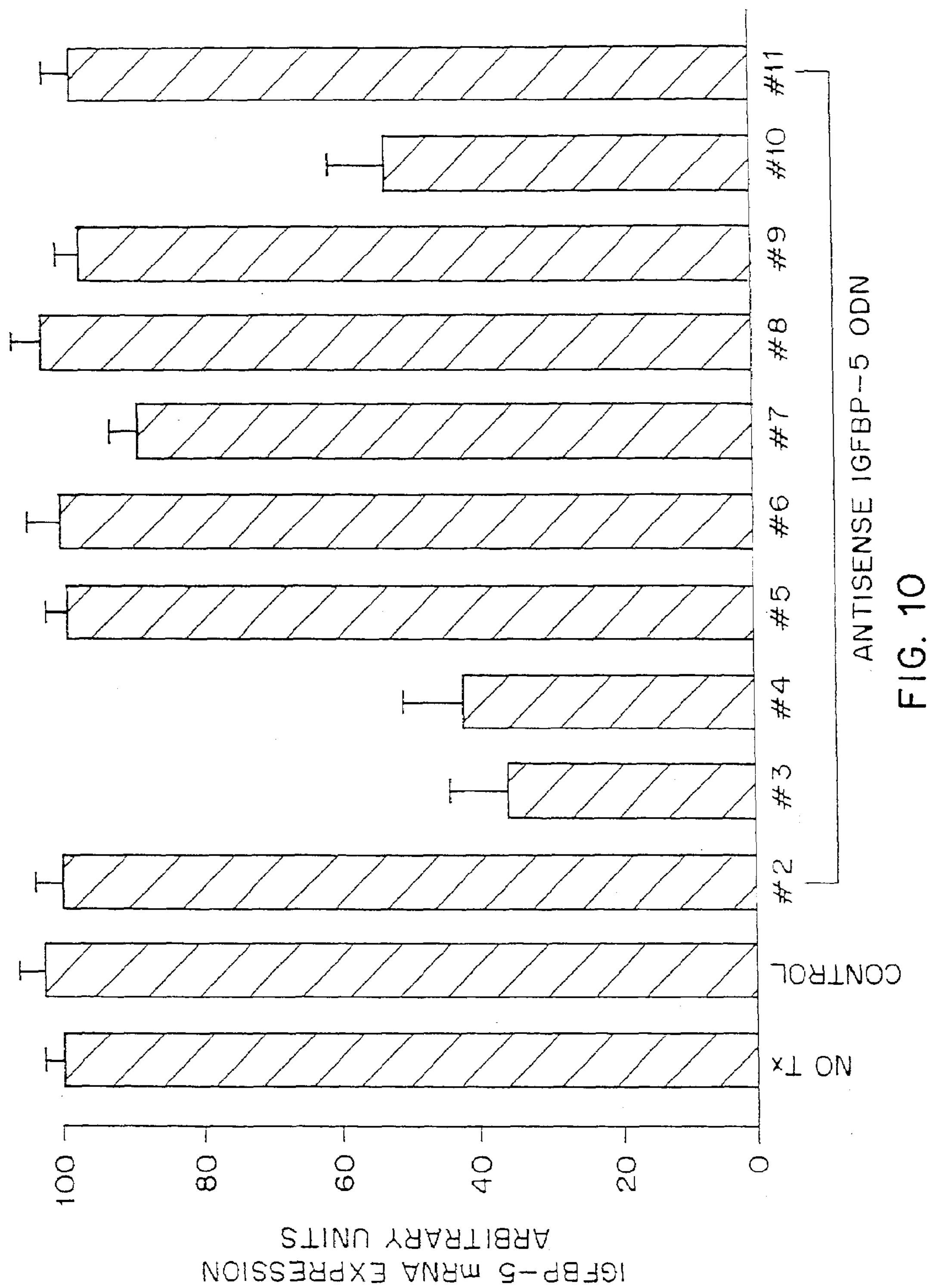
FIG. 10 shows a effect of each of the 10 antisense ODN's indicated in FIG. 9 on IGBFP-5 mRNA levels.

To identify appropriate antisense IGFBP-5 ODN sequences for use in human therapy, antisense ODN sequences directed against 10 different sites of the human IGFBP-5 gene (FIG. 9, Seq. ID Nos. 2-11) were synthesized and tested for their ability to decrease IGFBP-5 gene expression in human prostate cancer PC3 cells and LNCaP/T1 (LNCaP cells stably transfected to overexpress IGFBP-5) in in vitro cell culture. The results are summarized in FIG. 10. As shown, Seq. ID Nos. 3, 4 and 10 are active for reduction of IGFBP-5 expression, with Seq. ID No. 3 having the greatest potency. These three sequence overlap with or are immediately adjacent to the translation initiation or termination sites.

EXAMPLE 8

Metastatic prostate and breast cancer frequently invade bony tissue. Treatment of such metastases is very difficult, and progression of the cancer into the bone generally indicates a poor prognosis for long term survival. Thus, it would be desirable to have a methodology for inhibiting or delaying this progression. It was logical to assume that since IGF-1 and IGFBP-5 are important factors for growth of IGF-1 sensitive cancer, including in particular prostate and breast cancer, that the presence of high levels of IGFBP-5 in bone could be an important mechanism for promoting the growth and progression of metastatic lesions. Accordingly, Western analysis was performed on samples of primary human bone tissue obtained from patients suffering from metastatic prostate cancer. This experiment confirmed the presence of high levels of IGFBP-5 in bone. Inhibition of these levels using antisense IGFBP-5 ODN in accordance with the invention should provide an effective therapy for inhibiting or delaying the progression of metastatic lesions in the bone.

SEQUENCES

Seq. ID No. 1 GACCACGCTGATCACCAT

Seq. ID No. 2 GTCGCCCCCTTTACCTCG

Seq. ID No. 3 CGCGGTGAGCAACACCAT

Seq. ID No. 4 AGGTCATGCAGCAGCCGC

Seq. ID No. 5 GCTCGCGGTAGCTCTTTT

Seq. ID No. 6 TCTTTCTGCGGTCCTTCT

Seq. ID No. 7 TGCGTGGGCTGGCTTTGA

Seq. ID No. 8 CGTCAACGTACTCCATGC

Seq. ID No. 9 AGGGGGTGAGGGAAAGGT

Seq. ID No. 10 TCAAATAGATAGATATAT

Seq. ID No. 11 TACACAAACACTTCCTTC

Seq. ID No. 12 GACCACGCTCATGACCAT

Seq. ID No. 13 mouse IGFBP-5 nucleic acid sequence
gcagtctctt tggaaacttc taaaagagct aggaaagagc tgcaaagctg
tttgggcttt tttccccctt tttgttcctt tttgttaccc ccccctcgg tctgcaccct
tctccggact tcacgcagaa cctgcgggtt tcgaagaggt ggtgacagag
caggtgttgg ggtccaggtt tggtgaggtc tgggtttttg cccttttcc cccctc-
gatt tcaacatttt cccgatcttg ttgtcagccg ccgacgcctc ttacctgttc
tgcggcagca gcgcagctgg ccgctgagac cgagcggagt ggggttgcgt
tttagatttt aagcaaaggg gggaaaatta agcccaatcc attttttct tcacctc-
ctc ccttttcaag gcctccaagc taattatttc tgttgctttg gagtgagcaa ttct-
gtggtt ctctccacca ccaccccaa ttctgacccg atcccgcctg
ggggtttcta cggtctccgc tcgctctgcg tgcacctggc gcgcctcttt
ttttcacccc caacctgttg caagtcttta atcctcgcaa ttgggacttg cgtg-
caggca tctgaatcct ccttgcctca tattttgcaa gtgtttgggg gagagcacct
gctctacctg caagagattt aaaaggaaaa aaatctccag gctccctctt tctc-
cacaca ctctcgctct cctgccccgc cccgaggtaa agccagactc
cgagaaaatg gtgatcagcg tggtcctcct gctgctggcc gcctatgccg tac-
cggctca aggcctgggt tctttcgtgc actgtgaacc ctgcgacgag
aaagctctgt ccatgtgtcc ccccagccct ctgggctgtg agctggtcaa
agagcccggc tgtggctgct gcatgacttg cgccctggcg gagggacagt
cgtgtggcgt ctacacggag cgctgcgccc agggtttgcg ctgcctcccc
cggcaggatg aggagaagcc gctgcacgcc ctgctgcacg gccgcggggt
ttgcctcaac gaaaagagct acggcgagca aaccaagata agagactctc
gggaacacga ggaacccacc acctccgaga tggctgaaga gacctactcc
cccaaggtct tccggcccaa gcacactcgc atttccgagc tgaaggctga
ggctgtgaag aaggaccgca gaaagaagct gacccagtcc aagtttgtgg
ggggtgcaga gaacactgcc caccccagag tcatccctgc acctgagatg
agacaggaat ccgaacaagg cccctgccgc agacacatgg aagcttccct
ccaggagttc aaagccagcc cacgcatggt gccccgtgct gtgtacctgc
ccaactgtga ccgcaaagga ttctacaaga gaaagcagtg taagccctcc
cgtggccgca aacgtggcat ctgctggtgt gtggacaagt acggaatgaa
gctgccgggc atggagtacg tggatgggga ctttcagtgc cacgccttcg
acagcagtaa cgttgagtga cgcgtcccct cccttcctcc ccctatccta
cccccccagc cccaactcca gccagcgcct ccctccaccc caggacgtca ctcatttcat ctcatttagg ggaaatatat atacatatat atttgaggaa actgag-
gacc tcggaatctc tagcaagggc taaggagaca ctccccacca tgac-
cccgga aatgtattcc tttttgaagc aagttgaacg gacagagaag ggaag-
gagag aagaagcaag agggagcgag agatggaaag aaagcaaagc
gttggaatag aggaaaagag ggaaggacag ataggattag agagagaaga
gagaaacagc aaggcagaaa ggactccaca accaaggctg aatctgccct
tttgctttca gctctagcct ggggtcagaa aaagtgtggc attcagtgac
acccagttta gattggtcaa ggggagaaaa gaaacaaggt gtgtcagtgc
ctctcgggtc tgtcccctcc tgcagccagc agtgtggatg gctagacccc
tcaccctcct ctcctcttac ccaagtgcag ggtgatttca tccccaaatt tacaaa-
gact aaaatgcatt ccatccctct gaaaataaac aaaagtgagt gattgaagat
aggttttccc ccagcagaca agtgaactca gaatgtgtgc aaattttact cttgt-
taaag atttttttaa gaagtcagta cgcacccccca acactggaaa gacttgattc
tccagggtga caagcaattc agaagcgcgt ggcttcggcc cttgatttca cta-
gactcaa agctggcccg gcagcctctg tggaggagga tgagaggtgg
agaaaaccaa ggggcttgta ctcacccaca agactccatg tagactttat
aggcatataa atctattttc tttacctttt tttccctttc cctttctttc gaagttttgc
attacctctt taaagtagtt ttttttagga cactgaagat cttcctcatt ctgg-
gaaaaa tccatatttc acaaatacaa cccagaacgc cagcttggcc tgcgtc-
cagg cagcctttct cgtgagctac aagtgtggct cttttgtggg gcaccgattt
ggatcttctc atgattccaa acgtgtgttg aagtgaatcc accaagccag
gtaactgcca gcacccaagg gtgcatcaag tgcatagccc aggtcacccc
atttcagcct tccaacccgc agaaagtaac tgtctcacac cacaccacat aaac-
ctgcca gatccatctg taacccactg gcctgcccag accttttttt cccatctgca
ttttttttt tgaactgcat tttgaaagcc tccctcagat gccaggctga cagatca-
gag agaaactaac atgagagatg acagaggagg aggaagtgga
gggtgggggc agagacttcc acagagagac atagaagatg gagcagaggt
ctgggggtgg ggaggacaag aaagagacag agagaggaaa ataccaatag
aattttcctt ggtgtctccc atctaatcaa ctctctgaga tttgagagga aaaa-
gaaggc aggggaagaa cttgaggtag aaatgaggtc agttcaagtc
acagggccca gatggtgggt aactgaggca ggatccaaaa aaaatactta
tgctttttac tggtgaaaca gattgaaaaa aaaattgaac aacaaaccag tttgt-
gaaaa aaaaaaatgg gaaaaaaaat caccccgatg tggaagagct cggctc-
ctct ttagcatttt ggtacttaag gaaataaaaa agaaaaacct ggaagatctc
acattttatt acaaagtga Seq. ID No. 14 human IGFBP-5 nucleic acid sequence
ctctcctgcc ccaccccgag gtaaaggggg cgactaagag aagatggtgt
tgctcaccgc ggtcctcctg ctgctggccg cctatgcggg gccggcccag
agcctgggct ccttcgtgca ctgcgagccc tgcgacgaga aagccctctc cat-
gtgcccc cccagccccc tgggctgcga gctggtcaag gagccgggct gcg-
gctgctg catgacctgc gccctggccg aggggcagtc gtgcggcgtc tacac-
cgagc gctgcgccca ggggctgcgc tgcctccccc ggcaggacga
ggagaagccg ctgcacgccc tgctgcacgg ccgcggggtt tgcctcaacg
aaaagagcta ccgcgagcaa gtcaagatcg agagagactc ccgtgagcac
gaggagccca ccacctctga gatggccgag gagacctact cccccaagat
cttccggccc aaacacaccc gcatctccga gctgaaggct gaagcagtga
agaaggaccg cagaaagaag ctgacccagt ccaagtttgt cgggggagcc
gagaacactg cccacccccg gatcatctct gcacctgaga tgagacagga
gtctgagcag ggcccctgcc gcagacacat ggaggcttcc ctgcaggagc
tcaaagccag cccacgcatg gtgccccgtg ctgtgtacct gcccaattgt gac-
cgcaaag gattctacaa gagaaagcag tgcaaacctt cccgtggccg
caagcgtggc atctgctggt gcgtggacaa gtacgggatg aagctgccag
gcatggagta cgttgacggg gactttcagt gccacacctt cgacagcagc
aacgttgagt gatgcgtccc cccccaacct ttccctcacc ccctcccacc
cccagccccg actccagcca gcgcctccct ccaccccagg acgccactca
tttcatctca tttaagggaa aaatatatat ctatctattt gaggaaactg aggac-
ctcgg aatctctagc aagggctcaa cttcgaaaat ggcaacaaca gagatg-
caaa aagctaaaaa gacacccccc ccctttaaat ggttttcttt ttgaggcaag
ttggatgaac agagaaggga agagaggaag aacgagagga agagaaggga
aggaagtgtt tgtgtagaag agagagaaag acgaatagag ttaggaaaag
gaagacaagc aggtgggcag gaaggacatg caccgagacc aggcaggggc
ccaactttca cgtccagccc tggcctgggg tcgggagagg tgggcgctag
aagatgcagc ccaggatgtg gcaatcaatg acactattgg ggtttcccag
gatggattgg tcagggggag aaaggaaaag gcaaaacact ccaggacctc
tcccggatct gtctcctcct ctagccagca gtatggacag ctggacccct
gaacttcctc tcctcttacc tgggcagagt gttgtctctc cccaaattta taaaaactaa aatgcattcc attcctctga aagcaaaaca aattcataat tgagtgatat taaatagaga ggttttcgga agcagatctg tgaatatgaa at SEQ ID No. 15. ttttttttttttttcaaa SEQ ID No. 16 atgatagatatatatttttc SEQ ID No. 17 ccttaaatgagatgaaatga SEQ ID NO. 18 gtggcgtcctggggtggagg SEQ ID NO. 19 gaggcgctggctggagtcgg SEQ ID NO. 20 ggctgggggtgggagggggt SEQ ID NO. 21 gagggaaaggttgggggggg SEQ ID NO. 22 acgcatcactcaacgttgct SEQ ID NO. 23 gctgtcgaaggtgtggcact SEQ ID NO. 24 gaaagtccccgtcaacgtac SEQ ID NO. 25 tccatgcctggcagcttcat SEQ ID NO. 26 cccgtacttgtccacgcacc SEQ ID NO. 27 agcagatgccacgcttgcgg SEQ ID NO. 28 ccacgggaaggtttgcactg SEQ ID NO. 29 ctttctcttgatgaatcctt SEQ ID NO. 30 tgcggtcacaattgggcagg SEQ ID NO. 31 tacacagcacggggcaccat SEQ ID NO. 32 gcgtgggctggctttgagct SEQ ID NO. 33 cctgcagggaagcctccatg SEQ ID NO. 34 tgtctgcggcaggggccctg SEQ ID NO. 35 ctcagactcctgtctcatct SEQ ID NO. 36 caggtgcagagatgatccgg SEQ ID NO. 37 gggtgggcagtgttctcggc SEQ ID NO. 38 tcccccgacaaacttggact SEQ ID NO. 39 gggtcagcttctttctgcgg SEQ ID NO. 40 tccttcttcactgcttcagc SEQ ID NO. 41 cttcagctcggagatgcggg SEQ ID NO. 42 tgtgtttgggccggaagatc SEQ ID NO. 43 ttgggggagtaggtctcctc SEQ ID NO. 44 ggccatctcagaggtggtgg SEQ ID NO. 45 gctcctcgtgctcacgggag SEQ ID NO. 46 tctctctcgatcttgacttg SEQ ID NO. 47 ctcgcggtagctcttttcgt SEQ ID NO. 48 tgaggcaaaccccgcggccg SEQ ID NO. 49 tgcagcagggcgtgcagcgg SEQ ID NO. 50 cttctcctcgtcctgccggg SEQ ID NO. 51 ggaggcagcgcagcccctgg SEQ ID NO. 52 gcgcagcgctcggtgtagac SEQ ID NO. 53 gccgcacgactgcccctcgg SEQ ID NO. 54 cctgggcgcaggtcatgcag SEQ ID NO. 55 cagccgcagcccggctcctt SEQ ID NO. 56 gaccagctcgcagcccaggg SEQ ID NO. 57 ggctgggggggcacatggag SEQ ID NO. 58 agggctttctcgtcgcaggg SEQ ID NO. 59 ctcgcagtgcacgaaggagc SEQ ID NO. 60 ccaggctctgggccggcccc SEQ ID NO. 61 gcataggcggccagcagcag SEQ ID NO. 62 gaggaccgcggtgagcaaca SEQ ID NO. 63 ccatcttctcttagtcgccc SEQ ID NO. 64 cctttacctcggggtggggc SEQ ID NO. 65 aggagagcgagagtgcaggg SEQ ID NO. 66 gaccgcggtgagcaacaccat

The invention claimed is:

1. A method for delaying progression of hormone-regulated mammalian tumor cells to an androgen-independent state, comprising treating hormone-sensitive mammalian tumor cells with an antisense oligonucleotide which inhibits expression of IGFBP-5 by the tumor cells.

2. The method of claim 1, wherein the tumor cells are prostatic tumor cells.

3. The method of claim 2, wherein the antisense oligonucleotide is complementary to a segment of IGFBP-5 mRNA, said segment including the translation initiation or termination site.

4. The method of claim 2, wherein the antisense oligonucleotide comprises a series of contiguous bases as set forth in SEQ ID No. 3, 4 or 10.

5. The method of claim 1, wherein the tumor cells are breast cancer cells.

6. The method of claim 1, wherein the antisense oligonucleotide is complementary to a segment of IGFBP-5 mRNA, said segment including the translation initiation or termination site.

7. The method of claim 1, wherein the antisense oligonucleotide comprises a series of contiguous bases as set forth in SEQ ID No. 3, 4 or 10.

8. A method for treating a hormone-responsive cancer in a mammalian individual suffering from hormone-responsive cancer, comprising the steps of initiating hormone-withdrawal to induce apoptotic cell death of hormone-responsive cancer cells in the individual, and administering to the individual a composition effective to inhibit expression of IGFBP-5 by the hormone-responsive cancer cells, thereby delaying the progression of hormone-responsive cancer cells to a hormone-independent state in the individual, wherein the composition effective to inhibit expression of IGFBP-5 is an antisense oligonucleotide.

9. The method of claim 8, wherein the antisense oligonucleotide is complementary to a segment of IGFBP-5 mRNA, said segment including the translation initiation or termination site.

10. The method of claim 8, wherein the antisense oligonucleotide comprises a series of contiguous bases as set forth in SEQ ID No. 3, 4, or 10.

11. The method of claim 8, wherein the hormone-responsive cancer is prostate cancer.

12. The method of claim 11, wherein the antisense oligonucleotide comprises a series of contiguous bases as set forth in SEQ ID No. 3, 4, or 10.

13. A method for inhibiting or delaying metastatic boney progression of an IGF-1 sensitive tumor in a mammal, comprising the step of administering to the mammal a composition effective to inhibit expression of IGFBP-5 by the hormone-responsive cancer cells, thereby inhibiting or delaying metastatic boney progression of the tumor, wherein the composition effective to inhibit expression of IGFBP-5 is an antisense oligonucleotide.

14. The method of claim 13, wherein the antisense oligonucleotide is complementary to a segment of IGFBP-5 mRNA, said segment including the translation initiation or termination site.

15. The method of claim 13, wherein the antisense oligonucleotide comprises a series of contiguous bases as set forth in SEQ ID No. 3, 4, or 10.

16. The method of claim 13, wherein the IGF-1 sensitive tumor is a prostate cancer.

17. The method of claim 16, wherein the antisense oligonucleotide comprises a series of contiguous bases as set forth in SEQ ID No. 3, 4, or 10.

18. A composition for treatment of hormone-regulated cancer comprising an antisense oligonucleotide which inhibits expression of IGFBP-5 by hormone-regulated tumor cells, wherein the antisense oligonucleotide is complementary to a segment of IGFBP-5 mRNA, said segment including the translation initiation or termination site.

19. A composition for treatment of hormone-regulated cancer comprising an antisense oligonucleotide which inhibits expression of IGFBP-5 by hormone-regulated tumor cells, wherein the antisense oligonucleotide comprises a series of contiguous bases as set forth in SEQ ID No. 3, 4 or 10.

20. The composition according to claim 18, wherein the antisense oligonucleotide has a length of from 15 to 30 nucleotides.

21. The method of claim 1, wherein the antisense is complementary to a portion of Seq. ID NO. 13 or 14.

22. The method of claim 3, wherein the antisense is complementary to a portion of Seq. ID NO. 13 or 14.

23. The method of claim 6, wherein the antisense is complementary to a portion of Seq. ID NO. 13 or 14.

24. The method of claim 8, wherein the antisense is complementary to a portion of Seq. ID NO. 13 or 14.

25. The method of claim 9, wherein the antisense is complementary to a portion of Seq. ID NO. 13 or 14.

26. The method of claim 11, wherein the antisense is complementary to a portion of Seq. ID NO. 13 or 14.

27. The method of claim 1, wherein the mammalian tumor cells are human tumor cells.

28. The method of claim 8, wherein the individual is a human.

29. The method of claim 13, wherein the mammal is a human.

* * * * *

```
                         SEQUENCE LISTING

<160> NUMBER OF SEQ ID NOS: 66

<210> SEQ ID NO 1
<211> LENGTH: 18
<212> TYPE: DNA
<213> ORGANISM: murine
<220> FEATURE:
<221> NAME/KEY: antisense IGFBP-5 oligodeoxynucleotide
<222> LOCATION: (1)..(18)

<400> SEQUENCE: 1

gaccacgctg atcaccat                                                18


<210> SEQ ID NO 2
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 2
```

-continued gtcgcccct ttacctcg 18

<210> SEQ ID NO 3
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 3
cgcggtgagc aacaccat 18

<210> SEQ ID NO 4
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 4
aggtcatgca gcagccgc 18

<210> SEQ ID NO 5
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 5
gctcgcggta gctctttt 18

<210> SEQ ID NO 6
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 6
tctttctgcg gtccttct 18

<210> SEQ ID NO 7
<211> LENGTH: 18
<212> TYPE: DNA
<213> ORGANISM: human

<400> SEQUENCE: 7
tgcgtgggct ggctttga 18

<210> SEQ ID NO 8
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 8
cgtcaacgta ctccatgc 18

-continued

<210> SEQ ID NO 9
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 9
agggggtgag ggaaaggt 18

<210> SEQ ID NO 10
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 10
tcaaatagat agatatat 18

<210> SEQ ID NO 11
<211> LENGTH: 18
<212> TYPE: DNA
<213> ORGANISM: human
<220> FEATURE:
<221> NAME/KEY: antisense IGFBP-5 oligodeoxynucleotide
<222> LOCATION: (1)..(18)

<400> SEQUENCE: 11
tacacaaaca cttccttc 18

<210> SEQ ID NO 12
<211> LENGTH: 18
<212> TYPE: DNA
<213> ORGANISM: murine
<220> FEATURE:
<221> NAME/KEY: mismatch control
<222> LOCATION: (1)..(18)

<400> SEQUENCE: 12
gaccacgctc atgaccat 18

<210> SEQ ID NO 13
<211> LENGTH: 3419
<212> TYPE: DNA
<213> ORGANISM: murine insulin-like growth factor binding protein-5

<400> SEQUENCE: 13
gcagtctctt tggaaacttc taaaagagct aggaaagagc tgcaaagctg tttgggcttt 60 tttcccctt tttgttcctt tttgttaccc cccccctcgg tctgcaccct tctccggact 120
tcacgcagaa cctgcgggtt tcgaagaggt ggtgacagag caggtgttgg ggtccaggtt 180
tggtgaggtc tgggtttttg cccttttttcc cccctcgatt tcaacatttt cccgatcttg 240
ttgtcagccg ccgacgcctc ttacctgttc tgcggcagca gcgcagctgg ccgctgagac 300
cgagcggagt ggggttgcgt tttagatttt aagcaaaggg gggaaaatta agcccaatcc 360 attttttttct tcacctcctc ccttttcaag gcctccaagc taattatttc tgttgctttg 420
gagtgagcaa ttctgtggtt ctctccacca ccacccccaa ttctgacccg atcccgcctg 480
ggggtttcta cggtctccgc tcgctctgcg tgcacctggc gcgcctcttt ttttcacccc 540
caacctgttg caagtcttta atcctcgcaa ttgggacttg cgtgcaggca tctgaatcct 600

-continued

```
ccttgcctca tattttgcaa gtgtttgggg gagagcacct gctctacctg caagagattt    660
aaaaggaaaa aaatctccag gctccctctt tctccacaca ctctcgctct cctgccccgc    720
cccgaggtaa agccagactc cgagaaaatg gtgatcagcg tggtcctcct gctgctggcc    780
gcctatgccg taccggctca aggcctgggt tctttcgtgc actgtgaacc ctgcgacgag    840
aaagctctgt ccatgtgtcc ccccagccct ctgggctgtg agctggtcaa agagcccggc    900
tgtggctgct gcatgacttg cgccctggcg gagggacagt cgtgtggcgt ctacacggag    960
cgctgcgccc agggtttgcg ctgcctcccc cggcaggatg aggagaagcc gctgcacgcc   1020
ctgctgcacg gccgcggggt ttgcctcaac gaaaagagct acggcgagca aaccaagata   1080
agagactctc gggaacacga ggaacccacc acctccgaga tggctgaaga gacctactcc   1140
cccaaggtct tccggcccaa gcacactcgc atttccgagc tgaaggctga ggctgtgaag   1200
aaggaccgca gaaagaagct gacccagtcc aagtttgtgg ggggtgcaga gaacactgcc   1260
caccccagag tcatccctgc acctgagatg agacaggaat ccgaacaagg cccctgccgc   1320
agacacatgg aagcttccct ccaggagttc aaagccagcc cacgcatggt gccccgtgct   1380
gtgtacctgc ccaactgtga ccgcaaagga ttctacaaga gaaagcagtg taagccctcc   1440
cgtggccgca aacgtggcat ctgctggtgt gtggacaagt acggaatgaa gctgccgggc   1500
atggagtacg tggatgggga ctttcagtgc cacgccttcg acagcagtaa cgttgagtga   1560
cgcgtcccct cccttcctcc ccctatccta cccccccagc cccaactcca gccagcgcct   1620
ccctccaccc caggacgtca ctcatttcat ctcatttagg ggaaatatat atacatatat   1680
atttgaggaa actgaggacc tcggaatctc tagcaagggc taaggagaca ctccccacca   1740
tgaccccgga aatgtattcc tttttgaagc aagttgaacg gacagagaag ggaaggagag   1800
aagaagcaag agggagcgag agatggaaag aaagcaaagc gttggaatag aggaaaagag   1860
ggaaggacag ataggattag agagagaaga gagaaacagc aaggcagaaa ggactccaca   1920
accaaggctg aatctgccct tttgctttca gctctagcct ggggtcagaa aaagtgtggc   1980
attcagtgac acccagttta gattggtcaa ggggagaaaa gaaacaaggt gtgtcagtgc   2040
ctctcgggtc tgtcccctcc tgcagccagc agtgtggatg gctagacccc tcaccctcct   2100
ctcctcttac ccaagtgcag ggtgatttca tccccaaatt tacaaagact aaaatgcatt   2160
ccatccctct gaaaataaac aaaagtgagt gattgaagat aggttttccc ccagcagaca   2220
agtgaactca gaatgtgtgc aaattttact cttgttaaag atttttttaa gaagtcagta   2280
cgcaccccca acactggaaa gacttgattc tccagggtga caagcaattc agaagcgcgt   2340
ggcttcggcc cttgatttca ctagactcaa agctggcccg gcagcctctg tggaggagga   2400
tgagaggtgg agaaaaccaa ggggcttgta ctcacccaca agactccatg tagactttat   2460
aggcatataa atctattttc tttacctttt tttccctttc cctttctttc gaagttttgc   2520
attacctctt taaagtagtt ttttttagga cactgaagat cttcctcatt ctgggaaaaa   2580
tccatatttc acaaatacaa cccagaacgc cagcttggcc tgcgtccagg cagcctttct   2640
cgtgagctac aagtgtggct cttttgtggg gcaccgattt ggatcttctc atgattccaa   2700
acgtgtgttg aagtgaatcc accaagccag gtaactgcca gcacccaagg gtgcatcaag   2760
tgcatagccc aggtcacccc atttcagcct tccaacccgc agaaagtaac tgtctcacac   2820
cacaccacat aaacctgcca gatccatctg taacccactg gcctgcccag accttttttt   2880
cccatctgca tttttttttt tgaactgcat tttgaaagcc tccctcagat gccaggctga   2940
cagatcagag agaaactaac atgagagatg acagaggagg aggaagtgga gggtgggggc   3000
```

-continued

```
agagacttcc acagagagac atagaagatg gagcagaggt ctgggggtgg ggaggacaag   3060

aaagagacag agagaggaaa ataccaatag aattttcctt ggtgtctccc atctaatcaa   3120

ctctctgaga tttgagagga aaaagaaggc aggggaagaa cttgaggtag aaatgaggtc   3180

agttcaagtc acagggccca gatggtgggt aactgaggca ggatccaaaa aaaatactta   3240

tgctttttac tggtgaaaca gattgaaaaa aaaattgaac aacaaaccag tttgtgaaaa   3300

aaaaaaatgg gaaaaaaaat caccccgatg tggaagagct cggctcctct ttagcatttt   3360

ggtacttaag gaaataaaaa agaaaaacct ggaagatctc acattttatt acaaagtga    3419
```

<210> SEQ ID NO 14
<211> LENGTH: 1612
<212> TYPE: DNA
<213> ORGANISM: human insulin-like growth factor binding protein-5

<400> SEQUENCE: 14

```
ctctcctgcc ccaccccgag gtaaaggggg cgactaagag aagatggtgt tgctcaccgc     60

ggtcctcctg ctgctggccg cctatgcggg gccggcccag agcctgggct ccttcgtgca    120

ctgcgagccc tgcgacgaga aagccctctc catgtgcccc cccagccccc tgggctgcga    180

gctggtcaag gagccgggct gcggctgctg catgacctgc gccctggccg aggggcagtc    240

gtgcggcgtc tacaccgagc gctgcgccca ggggctgcgc tgcctccccc ggcaggacga    300

ggagaagccg ctgcacgccc tgctgcacgg ccgcggggtt tgcctcaacg aaaagagcta    360

ccgcgagcaa gtcaagatcg agagagactc ccgtgagcac gaggagccca ccacctctga    420

gatggccgag gagacctact cccccaagat cttccggccc aaacacaccc gcatctccga    480

gctgaaggct gaagcagtga agaaggaccg cagaaagaag ctgacccagt ccaagtttgt    540

cgggggagcc gagaacactg cccacccccg gatcatctct gcacctgaga tgagacagga    600

gtctgagcag ggcccctgcc gcagacacat ggaggcttcc ctgcaggagc tcaaagccag    660

cccacgcatg gtgccccgtg ctgtgtacct gcccaattgt gaccgcaaag gattctacaa    720

gagaaagcag tgcaaacctt cccgtggccg caagcgtggc atctgctggt gcgtggacaa    780

gtacgggatg aagctgccag gcatggagta cgttgacggg gactttcagt gccacacctt    840

cgacagcagc aacgttgagt gatgcgtccc cccccaacct ttccctcacc ccctcccacc    900

cccagccccg actccagcca gcgcctccct ccaccccagg acgccactca tttcatctca    960

tttaagggaa aaatatatat ctatctattt gaggaaactg aggacctcgg aatctctagc   1020

aagggctcaa cttcgaaaat ggcaacaaca gagatgcaaa aagctaaaaa gacacccccc   1080

ccctttaaat ggttttcttt ttgaggcaag ttggatgaac agagaaggga agagaggaag   1140

aacgagagga agagaaggga aggaagtgtt tgtgtagaag agagagaaag acgaatagag   1200

ttaggaaaag gaagacaagc aggtgggcag gaaggacatg caccgagacc aggcaggggc   1260

ccaactttca cgtccagccc tggcctgggg tcgggagagg tgggcgctag aagatgcagc   1320

ccaggatgtg gcaatcaatg acactattgg ggtttcccag gatggattgg tcagggggag   1380

aaaggaaaag gcaaaacact ccaggacctc tcccggatct gtctcctcct ctagccagca   1440

gtatggacag ctggacccct gaacttcctc tcctcttacc tgggcagagt gttgtctctc   1500

cccaaattta taaaaactaa aatgcattcc attcctctga aagcaaaaca aattcataat   1560

tgagtgatat taaatagaga ggttttcgga agcagatctg tgaatatgaa at           1612
```

<210> SEQ ID NO 15

-continued

<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 15
tttttttttt ttttttcaaa 20

<210> SEQ ID NO 16
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 16
atgatagata tatatttttc 20

<210> SEQ ID NO 17
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 17
ccttaaatga gatgaaatga 20

<210> SEQ ID NO 18
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 18
gtggcgtcct ggggtggagg 20

<210> SEQ ID NO 19
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 19
gaggcgctgg ctggagtcgg 20

<210> SEQ ID NO 20
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 20
ggctgggggt gggagggggt 20

<210> SEQ ID NO 21
<211> LENGTH: 20

-continued

```
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 21

gagggaaagg ttgggggggg                                          20


<210> SEQ ID NO 22
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 22

acgcatcact caacgttgct                                          20


<210> SEQ ID NO 23
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 23

acgcatcact caacgttgct                                          20


<210> SEQ ID NO 24
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 24

gaaagtcccc gtcaacgtac                                          20


<210> SEQ ID NO 25
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 25

tccatgcctg gcagcttcat                                          20


<210> SEQ ID NO 26
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 26

cccgtacttg tccacgcacc                                          20


<210> SEQ ID NO 27
<211> LENGTH: 20
<212> TYPE: DNA
```

-continued

```
<213> ORGANISM: human
<220> FEATURE:
<221> NAME/KEY: antisense IGFBP-5 oligodeoxynucleotide
<222> LOCATION: (1)..(20)

<400> SEQUENCE: 27

agcagatgcc acgcttgcgg                                              20


<210> SEQ ID NO 28
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 28

ccacgggaag gtttgcactg                                              20


<210> SEQ ID NO 29
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 29

ctttctcttg atgaatcctt                                              20


<210> SEQ ID NO 30
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 30

tgcggtcaca attgggcagg                                              20


<210> SEQ ID NO 31
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 31

tacacagcac ggggcaccat                                              20


<210> SEQ ID NO 32
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 32

gcgtgggctg gctttgagct                                              20


<210> SEQ ID NO 33
<211> LENGTH: 20
<212> TYPE: DNA
<213> ORGANISM: human
```

<220> FEATURE:
<221> NAME/KEY: antisense IGFBP-5 oligodeoxynucleotide
<222> LOCATION: (1)..(20)

<400> SEQUENCE: 33
cctgcaggga agcctccatg 20

<210> SEQ ID NO 34
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 34
tgtctgcggc aggggccctg 20

<210> SEQ ID NO 35
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 35
ctcagactcc tgtctcatct 20

<210> SEQ ID NO 36
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 36
caggtgcaga gatgatccgg 20

<210> SEQ ID NO 37
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 37
gggtgggcag tgttctcggc 20

<210> SEQ ID NO 38
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 38
tcccccgaca aacttggact 20

<210> SEQ ID NO 39
<211> LENGTH: 20
<212> TYPE: DNA
<213> ORGANISM: human
<220> FEATURE:

```
<221> NAME/KEY: antisense IGFBP-5 oligodeoxynucleotide
<222> LOCATION: (1)..(20)

<400> SEQUENCE: 39

gggtcagctt ctttctgcgg                                              20


<210> SEQ ID NO 40
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 40

tccttcttca ctgcttcagc                                              20


<210> SEQ ID NO 41
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 41

cttcagctcg gagatgcggg                                              20


<210> SEQ ID NO 42
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 42

tgtgtttggg ccggaagatc                                              20


<210> SEQ ID NO 43
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 43

ttgggggagt aggtctcctc                                              20


<210> SEQ ID NO 44
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 44

ggccatctca gaggtggtgg                                              20


<210> SEQ ID NO 45
<211> LENGTH: 20
<212> TYPE: DNA
<213> ORGANISM: human
<220> FEATURE:
<221> NAME/KEY: antisense IGFBP-5 oligodeoxynucleotide
```

-continued

```
<222> LOCATION: (1)..(20)

<400> SEQUENCE: 45

gctcctcgtg ctcacgggag                                              20


<210> SEQ ID NO 46
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 46

tctctctcga tcttgacttg                                              20


<210> SEQ ID NO 47
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 47

ctcgcggtag ctcttttcgt                                              20


<210> SEQ ID NO 48
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 48

tgaggcaaac cccgcggccg                                              20


<210> SEQ ID NO 49
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 49

tgcagcaggg cgtgcagcgg                                              20


<210> SEQ ID NO 50
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 50

cttctcctcg tcctgccggg                                              20


<210> SEQ ID NO 51
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)
```

-continued

<400> SEQUENCE: 51
ggaggcagcg cagcccctgg 20

<210> SEQ ID NO 52
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 52
gcgcagcgct cggtgtagac 20

<210> SEQ ID NO 53
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 53
gccgcacgac tgcccctcgg 20

<210> SEQ ID NO 54
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 54
cctgggcgca ggtcatgcag 20

<210> SEQ ID NO 55
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 55
cagccgcagc ccggctcctt 20

<210> SEQ ID NO 56
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 56
gaccagctcg cagcccaggg 20

<210> SEQ ID NO 57
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 57
ggctgggggg gcacatggag 20

<210> SEQ ID NO 58
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 58
agggctttct cgtcgcaggg 20

<210> SEQ ID NO 59
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 59
ctcgcagtgc acgaaggagc 20

<210> SEQ ID NO 60
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 60
ccaggctctg ggccggcccc 20

<210> SEQ ID NO 61
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 61
gcataggcgg ccagcagcag 20

<210> SEQ ID NO 62
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 62
gaggaccgcg gtgagcaaca 20

<210> SEQ ID NO 63
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 63

-continued

```
ccatcttctc ttagtcgccc                                                   20


<210> SEQ ID NO 64
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 64

cctttacctc ggggtggggc                                                   20


<210> SEQ ID NO 65
<211> LENGTH: 20
<212> TYPE: DNA
<213> ORGANISM: human
<220> FEATURE:
<221> NAME/KEY: antisense IGFBP-5 oligodeoxynucleotide
<222> LOCATION: (1)..(20)

<400> SEQUENCE: 65

aggagagcga gagtgcaggg                                                   20


<210> SEQ ID NO 66
<211> LENGTH: 21
<212> TYPE: DNA
<213> ORGANISM: human
<220> FEATURE:
<221> NAME/KEY: antisense IGFBP-5 oligodeoxynucleotide
<222> LOCATION: (1)..(21)

<400> SEQUENCE: 66

gaccgcggtg agcaacacca t                                                 21
```